United States Patent [19]

Kogan et al.

[11] Patent Number: 5,186,930
[45] Date of Patent: Feb. 16, 1993

[54] SUSTAINED RELEASE ORAL SUSPENSIONS

[75] Inventors: Patricia W. Kogan, Union, N.J.; Edward M. Rudnic, Boca Raton, Fla.; Joel A. Sequeira, New York, N.Y.; Imtiaz A. Chaudry, Denville, N.J.

[73] Assignee: Schering Corporation, Kenilworth, N.J.

[21] Appl. No.: 630,122

[22] Filed: Dec. 19, 1990

Related U.S. Application Data

[62] Division of Ser. No. 270,311, Nov. 14, 1988, Pat. No. 4,999,189.

[51] Int. Cl.$^5$ ............ A61K 31/74; A61K 47/34
[52] U.S. Cl. ............ 424/78.1; 424/494; 424/495; 424/497; 424/498
[58] Field of Search ............ 424/79, 502, 483, 402, 424/583, 494, 495, 497, 498, 78.1

[56] References Cited

U.S. PATENT DOCUMENTS

| 3,138,525 | 6/1964 | Koff | 424/79 |
| 4,221,778 | 9/1980 | Raghunathan | 424/79 |
| 4,762,709 | 8/1988 | Sheumaker | 424/79 |
| 4,847,077 | 7/1989 | Raghunathan | 424/79 |
| 4,882,154 | 11/1989 | Yang et al. | 424/502 |
| 4,894,224 | 1/1990 | Sharma et al. | 424/502 |

FOREIGN PATENT DOCUMENTS

| 0249949 | 12/1978 | European Pat. Off. | |
| 0139881 | 5/1985 | European Pat. Off. | |
| 0171528 | 2/1986 | European Pat. Off. | |
| 0254811 | 2/1988 | European Pat. Off. | |
| 0254822 | 2/1988 | European Pat. Off. | |
| 2246037 | 4/1974 | Fed. Rep. of Germany | 424/79 |
| 0869149 | 5/1961 | United Kingdom | 424/79 |
| 1218102 | 1/1971 | United Kingdom | 424/79 |

Primary Examiner—Thurman K. Page
Assistant Examiner—P. Kulkosky
Attorney, Agent, or Firm—Thomas D. Hoffman

[57] ABSTRACT

Stable sustained release wax- and polymer-coated drug-ion exchange resin complexes especially useful in preparing oral suspensions are disclosed.

15 Claims, No Drawings

SUSTAINED RELEASE ORAL SUSPENSIONS

This is a division of application Ser. No. 270,311, filed Nov. 14, 1988, now U.S. Pat. No. 4,999,189.

FIELD OF THE INVENTION

The present invention relates to stable sustained release pharmaceutical compositions wherein at least one drug is bound to an ion-exchange resin.

BACKGROUND ART

Liquid pharmaceutical compositions comprising a drug bound to an ion exchange resin have been known for many years. For instance, British patent 869,149 discloses the adsorption of ionizable drugs on ion-exchange resins and the dispersion of the resultant solids in a carrier liquid, and German patent 2,246,037 discloses drug adsorbed on resin particles, which loaded resin particles are then coated with a water-insoluble film-forming resin such as a polyacrylic acid ester. Solid compositions comprising ion-exchange resins are disclosed, for example, in EP 249,949 to Sellassie et al.

More recent publications disclose further treatment of drug-ion-exchange resin particles in order to improve sustained release characteristics. For example, U.S. Pat. No. 4,221,778 to Raghunathan discloses ion exchange resin-drug complexes treated with an impregnating agent such as polyethylene glycol or propylene glycol prior to coating with a water-permeable diffusion barrier such as ethylcellulose; the impregnating treatment is said to prevent swelling and fracturing of the resin particle in solutions and to improve coatability. EP 171,528 to the same inventor discloses a similar resin treatment using glycerine to improve coatability. EP 254,811 and EP 254,822 both to Raghunathan and Chow, disclose similar impregnation of sulfonic cation exchange resins with agents such as hydroxypropylmethylcellulose and with high molecular weight polymers, respectively, to improve coatability. EP 139,881 to Shuemaker discloses compositions in which all ionic components having the same charge are present as resin complexes, thereby overcoming variations in the dissolution profile caused by ionic substances in the formulation.

SUMMARY OF THE INVENTION

The present invention relates to stable sustained release pharmaceutical compositions comprising a drug-resin complex suspended in a liquid carrier for oral administration. The drug-resin complex comprisese a drug-resin particle coated with a first inner coating of a wax and a second outer coating of a polymer, wherein said drug-resin particle comprises an acidic or basic drug ionically bound to an ion-exchange resin particle.

In addition, drug-resin complexes of the present invention may be used in combination products, e.g., where two or more drugs are used to prepare different drug-resin complexes to be combined in the suspension, or where one or more drugs are provided as drug-resin complexes and one or more drugs are dissolved in the liquid carrier.

In particular, the present invention relates to a pharmaceutical sustained release oral suspension comprising coated pseudoephedrine-ion exchange resin particles suspended in a liquid carrier further comprising loratadine.

DETAILED DESCRIPTION

In an effort to overcome stability problems associated with previously known polymer-coated resin particles arising from leaching of drug through the polymer coating and from drug dumping caused by swelling of the resin and subsequent cracking of the polymer coating, we have found that an inner water-insoluble wax coating applied to the drug-ion exchange resin particle, followed by an outer water-insoluble polymer coating, provides especially stable drug complexes.

The drug is bound to the ion exchange resin by an acid-base reaction. Either a cation or an anion exchange resin can be used, depending on whether the drug to be bound is acidic or basic, i.e., a basic drug is bound to a cation exchange resin and an acid drug is bound to an anion exchange resin. The resin is preferably maximally loaded with drug, but loading may be adjusted to provide the desired dose. Loading of drug on the resin can be accomplished by well known techniques, e.g., batchwise loading wherein a drug solution is mixed with resin in a suitable container for the time necessary to obtain maximal loading, or a solution of the drug can be passed through a column of resin until loading is complete. The drug-resin complex is preferably dried before coating.

Any ion exchange resin can be used to prepare the drug complex, provided it is pharmaceutically acceptable and has a suitable particle size or bead diameter. Preferred are resin particles with a size of about 75 to about 600 m. Typical resins are styrene-divinylbenzene resins such as Dowex 50 cation exchange resins.

The wax used to coat the resultant drug-resin particle is a high temperature melting, pharmaceutically acceptable water-insoluble wax or waxy substance such as a saturated fat, for example, carnauba wax, white wax, glyceryl monostearate, glyceryl oleate, paraffin or spermaceti, with carnauba wax being preferred. The wax is applied by a solvent, hot melt or spray coating method, all of which methods are well known in the art. The hot melt method, wherein molten wax is sprayed onto fluidized resin, is preferred. The wax coating represents about 3 to about 50%, preferably about 10 to about 25% of the weight of the wax coated drug-resin particle (i.e. the wax-coated particle).

The outer coating of water-insoluble polymer comprises a pharmaceutically acceptable polymer such as ethylcellulose, methylcellulose, hydroxypropylmethylcellulose (HPMC), hydroxyethylcellulose (HEC), acrylic acid ester, cellulose acetate phthalate, HEC phthalate, HPMC phthalate or other cellulosic polymers, or mixtures of polymers, with ethylcellulose being preferred. A plasticizer such as dibutylsebacate, vegetable oil, diethylsebacate, diethylphthalate, tricetin or propylene glycol is preferably included in the outer coating, with dibutylsebacate being preferred. The polymer coating represents about 5 to 60%, preferably about 25 to about 50% of the weight of the final coated drug-resin particle (i.e., the polymer-wax-coated particle); the plasticizer represents about 10 to about 25%, preferably about 15 to about 25%, more preferably about 20% of the polymer concentration. The polymer-plasticizer coating can be applied using conventional methods, preferably a spray coating method employing bottom spray fluidized bed equipment.

Any acidic or basic drug which can be bound to an ion exchange resin can be used. The invention is particularly well suited to water-soluble drugs, but can also be used for water-insoluble drugs. Examples of suitable drugs are decongestants, antihistamines, analgesics, antihypertensives, anticholinergics, antibiotics, antiinflammatories and antidepressants, with decongestants and antihistamines being preferred. Examples of particular drugs are pseudoephedrine, phenylpropanolamine, dextromethorphan, propranolol, codeine, ephedrine and chlorpheniramine. Pseudoephedrine is particularly preferred.

The liquid carrier in which drug-resin particles of the present invention are suspended optionally comprises pharmaceutically acceptable excipients well known in the art. Typical ingredients include sweeteners, preferably non-charged, highly concentrated sweeteners which allow the use of a lower volume of carrier, e.g., high fructose corn syrup such as Isosweet 5500; preservatives such as methylparaben, propylparaben or combinations thereof; and emulsifying agents such as Tween 80 or Tween 60. Also, the carrier preferably comprises one or more thickening agents such as guar gum or xanthan gum; one or more humectants such as propylene glycol or glycerin; flavoring agent(s); coloring agent(s); and opacifier(s) such as titanium dioxide.

Drug-resin complexes of the present invention can be used to prepare pharmaceutical compositions comprising a combination of drugs. For example, two or more drugs can be separately bound to ion exchange resins and separately coated, and the different drug-resin complexes can be added to the same liquid carrier, or drug-resin complexes comprising one or more drugs can be suspended in a liquid carrier in which one or more drugs are dissolved. This is especially useful for combinations wherein a fast-acting drug is bound to ion exchange resin and an inherently long-acting drug is dissolved in the liquid carrier. A combination may also comprise the same drug both as a drug-resin complex and as an uncoated drug-resin particle or in solution to provide both immediate and sustained release.

The rate of exchange of the drug is controlled by the thickness of the wax and polymer coatings, and therefore the coating thickness can be changed to vary the release rate to obtain the optimum dissolution and bioavailability profile for different drugs. Also, for a given drug, drug-resin particles with different coating thicknesses may be incorporated in the same suspension in order to provide controlled release of the active over the desired dosage time. The thickness of the coating and the percentage by weight of the coatings are clearly related e.g. a greater thickness requires a higher % by weight; the following table indicates coating concentrations necessary to produce slow and fast dissolutions rates for a pseudoephedrine-resin complex:

| Dissolution Rate | EXCIPIENT | | |
| --- | --- | --- | --- |
| | Wax | Dibutylsebacate | Ethylcellulose |
| slow | 11–15% | 6–10% | 40–44% |
| fast | 4–8% | 6–10% | 40–44% |

Pseudoephedrine, a well known and widely used nasal decongestant, is a preferred drug for preparing a drug-resin complex of the present invention.

A preferred composition of the present invention comprises a combination of pseudoephedrine-resin complexes having different coating thicknesses suspended in a liquid carrier also comprising the antihistamine loratadine or its decarbalkoxylation product, 6-chloro-6,11-dihydro-11-(4-piperidylidene)-5H-benzo[5,6] cyclohepta[1,2-b]pyridine, wherein the coated pseudoephedrine complex is present at about 7 to about 40 mg/ml, an amount sufficient to provide 5 to 15 mg pseudoephedrine/ml carrier, and wherein the loratadine or its decarbalkoxylation product is present at 0.5 to 1.0 mg/ml carrier. Loratadine is claimed in U.S. Pat. No. 4,282,233 and the decarbalkoxylation product is claimed in U.S. Pat. No. 4,659,716.

The following example demonstrates a four-part preparation of a preferred combination of the present invention. Parts I-III relate to the preparation of a pseudoephedrine-ion exchange complex, and Part IV describes the preparation of the liquid carrier. Those skilled in the art will recognize that other drugs may be similarly formulated.

EXAMPLE 1

Part I

| Ingredient | Amount |
| --- | --- |
| Dowex 50 WX8 Cation Exchange Resin (Acid Form) | 1.0 kg |
| Pseudoephedrine Free Base (PSE) | 500 grams |
| Hot sterile water | 50 liters |
| Alcohol USP | 2 liters |
| Yield: 1500 g Pseudoephedrine-Resin Complex | |

1. Charge 4 kg Dowex 50 WX8 cation exchange resin acid form to a suitable vessel equipped for agitation (e.g., polypropylene buckets and lightening mixers).
2. Add 10 liters of hot sterile water to the vessel and mix for one hour.
3. Allow the resin to settle, decant off the water and repeat Steps 2 and 3 one more time.
4. Repeat Steps 2 and 3 using one liter of alcohol USP instead of water.
5. Spread resin out on drying trays and let alcohol evaporate.
6. Dry the resin on drying trays to a constant weight in a suitable oven.
7. Use 1 kg of the washed and dried resin per container. Add 10 l of hot sterile water and 500 grams of pseudoephedrine base to the resin and mix for 72 hours. The ratio of resin to water to pseudoephedrine base must be maintained at 2:20:1 to get the maximum loading of 37.5% pseudoephedrine and 62.5% resin.
9. Wash the PSE-resin complex with sterile water as in Steps 1-3.
10. Wash the PSE-resin complex with alcohol as in Step 4.
11. Spread the resin on drying trays and let the ethanol evaporate.
12. Dry the PSE-resin complex on drying trays to a constant weight in a suitable drying oven.

Part II

| Ingredient | Amount |
| --- | --- |
| Pseudoephedrine-Resin Complex (Part I) | 650 g |
| Carnauba Wax | 130 g |
| Yield: 780 g Wax coated PSE-resin complex | |

1. Take 650 grams of PSE-resin complex from Part I and fluidize in a fluid bed coater (e.g. from Glatt Air Techniques) equipped with a Wurster column and a coaxial nozzle suitable for hot melt coatings. The coater must have a chamber filter housing and shakers, and must be well grounded to avoid static problems, or the resin will not fluidize. Fluidize for only 3-5 minutes before hot melt spraying begins.
2. Melt 3-4 kg carnauba wax in a stainless steel jacketed vessel equipped with an agitator. Spray 130 g of molten wax onto the resin using a pulse wax melter and pump equipped with a flowmeter, and a temperature exchanger to heat the atomizing air, or similar equipment.

Part III

| Ingredient | Amount |
|---|---|
| Wax coated PSE-resin complex (from Part II) | 650 g |
| Ethylcellulose | 542 g |
| Dibutylsebacate | 108 g |
| Alcohol USP (evaporates) | 4.82 kg |
| Sterile Water (evaporates) | 542 g |
| Yield: 1300 g finished coated particles | |

1. Add water and alcohol to a suitable vessel equipped for agitation.
2. Dissolve the dibutylsebacate in the solution of Step 1.
3. While mixing, add the ethylcellulose to the solution of Step 2. Mix overnight until a uniform solution is produced. The weight percentages of alcohol to water to ethylcellulose to dibutylsebacate must be maintained at 80.2%: 9%:9%:1.8%.
4. Apply all of the ethylcellulose solution to the wax coated PSE-resin matrix at 4-5 mls/min, using the fluid bed technique in a fluid bed coater equipped with a Wurster column.
5. Sieve through 40 mesh screen.
6. Fill the appropriate amount of uncoated (Part I) and coated (Part III) particles equal to 9.24 mg/ml pseudoephedrine base (equal to 10 mg/ml pseudoephedrine sulfate) into an amber glass bottle.

Part IV—Syrup Vehicle Formulation

| Ingredient | Amount mg/ml |
|---|---|
| Isosweet 5500 (High Fructose Corn Syrup from Staley Corp.) | 1018.00 |
| Propylene Glycol | 67.50 |
| Water | qs |
| Tween 80 | 6.75 |
| Glycerin | 133.00 |
| Methyl Paraben | 0.50 |
| Propyl Paraben | 0.10 |
| Titanium Dioxide | 6.75 |
| FD & C Yellow #6 | 0.04 |
| Peach Flavor | 1.00 |
| Xanthan Gum | 2.00 |
| Loratadine, micronized | 0.50 |

1. Charge corn syrup and propylene glycol to a suitable container.
2. Dissolve Tween 80 in water. Disperse xanthan gum in this solution. Add Step 2 to Step 1 and mix well.
3. Disperse parabens and loratadine in glycerin and add to Step 2, mix well.
4. Add titanium dioxide, peach flavor and yellow dye to Step 3. Homogenize until uniform (approximately 2 minutes).
5. Add desired amount of syrup to the beads in Step 6, Part III and mix well.

The final product, in addition to the syrup vehicle components listed above, contains:

| Ingredient | Amount mg/ml |
|---|---|
| PSE | 9.24 |
| Dowex resin | 15.68 |
| Carnauba wax | 3.44 |
| Dibutylsebacate | 4.71 |
| Ethylcellulose | 23.65 |

The pharmaceutical composition described above is administered at a rate of about 2.5 to about 10 ml per dose given 1 to 2 times a day. Those skilled in the art will recognize that dosage levels vary according to such factors as the age, weight and condition of the patient. Similar formulations comprising different drugs will be formulated and administered according to the usual daily dosages of the individual drugs.

We claim:

1. A stable sustained release drug-resin complex for use in liquid carrier for oral administration comprising a drug-resin particle coated with a first inner coating of a high temperature melting water-insoluble pharmaceutically acceptable wax and a second outer coating of a pharmaceutically acceptable water-insoluble polymer, wherein said drug-resin particle comprises an acidic or basic drug ionically bond to a pharmaceutically acceptable ion exchange resin particle and wherein the amount of the first inner coating is sufficient to prevent the resin in the drug-resin particle from swelling and cracking the second outer coating thereby releasing drug when said complex is placed in said liquid carrier.

2. A drug-resin complex of claim 1 wherein the wax coating represents about 3 to about 50% by weight of the wax-coated particle, and wherein the polymer represents about 5 to about 60% of the polymer-wax-coated particle.

3. A drug-resin complex of claim 2 wherein the wax coating represents about 10% to about 25% of the weight of the wax-coated particle and the polymer represents about 25% to about 50% of the weight of the polymer-wax-coated particle.

4. A drug-resin complex of claim 2 further comprising a plasticizer, wherein the plasticizer represents about 6 to about 25% of the polymer weight.

5. A drug-resin complex of claim 3 further comprising a plasticizer, wherein the plasticizer represents about 20% of the polymer weight.

6. A drug-resin complex of claim 1 wherein the drug is a decongestant or an antihistamine.

7. A drug-resin complex of claim 6 wherein the drug is selected from the group consisting of pseudoephedrine, phenylpropanolamine and chlorpheniramine.

8. A drug-resin complex of claim 1 wherein the wax is selected from the group consisting of carnauba wax, white wax, glyceryl monostearate, glyceryl oleate, paraffin and spermaceti.

9. A drug-resin complex of claim 1 wherein the polymer is selected from the group consisting of ethylcellulose, methylcellulose, hydroxypropylmethylcellulose and the phthalate thereof, hydroxyethylcellulose and the phthalate thereof, acrylic acid esters, cellulose acetate phthalate and mixtures thereof.

10. A drug-resin complex of claim 1 wherein the ion exchange resin is a styrene-divinylbenzene resin.

11. A drug-resin complex of claim 5 wherein the wax is carnauba wax, the polymer is ethylcellulose, and the ion-exchange resin is styrene-divinylbenzene.

12. A drug-resin complex of claim 11 wherein the drug is pseudoephedrine.

13. A sustained release pharmaceutical composition comprising:
a) 5 to 15 mg pseudoephedrine present as a pseudoephedrine resin complex comprising pseudoephedrine-cation exchange resin particles coated with a first inner coating comprised of a pharmaceutically acceptable wax and a second outer coating of a pharmaceutically acceptable water-insoluble polymer and a pharmaceutically acceptable plasticizer, wherein said pseudoephedrine-cation exchange particles comprise pseudoephedrine ionically bound to a pharmaceutically acceptable cation exchange resin particle; and
b) 0.5 to 1.0 mg loratadine or 6-chloro-6,11-dihydro-11-(4-piperidylidene)-5H-benzo[5,0]-cyclohepta[1,2-b]pyridine;
c) per ml of a pharmaceutically acceptable liquid carrier.

14. A composition of claim 13 wherein the cation exchange resin is a styrene-divinylbenzene resin, the wax is carnauba wax, the polymer is ethylcellulose, and the plasticizer is dibutylsebacate.

15. A composition of claim 13 comprising 9.24 mg pseudoephedrine, 15.68 mg styrene-divinylbenzene resin, 3.44 mg carnauba wax, 4.71 mg diethylsebacate, 23.65 mg ethylcellulose and 0.5 mg loratadine per ml carrier.

* * * * *